US005997495A

United States Patent [19]

Cook et al.

[11] Patent Number: 5,997,495

[45] Date of Patent: Dec. 7, 1999

[54] MEDICAL DEVICE FOR THE HAND

[75] Inventors: Gordon John Cook; Ian Graham Brown; Paul Gerard Gregory, all of Hants, United Kingdom

[73] Assignee: Novamedix Distribution Ltd, Nicosia, Cyprus

[21] Appl. No.: 08/947,934

[22] Filed: Oct. 9, 1997

[51] Int. Cl.[6] .......... A61F 5/00

[52] U.S. Cl. .......... 602/62; 602/13

[58] Field of Search .......... 602/5, 13, 212, 602/83, 26, 60–65; 601/22, 149; 128/DIG. 20, 672, 686, 877, 878; 606/201–204

[56] References Cited

U.S. PATENT DOCUMENTS

| | | | |
|---|---|---|---|
| 2,880,721 | 4/1959 | Corcoran . | |
| 5,354,260 | 10/1994 | Cook | 602/13 |
| 5,727,559 | 3/1998 | Hynson | 602/13 X |

FOREIGN PATENT DOCUMENTS

| | | |
|---|---|---|
| 0344949 | 12/1989 | European Pat. Off. . |
| WO9312708 | 7/1993 | WIPO . |

*Primary Examiner*—Richard J. Apley
*Assistant Examiner*—Kim M. Lee
*Attorney, Agent, or Firm*—Hopgood, Calimafde, Kalil & Judlowe

[57] ABSTRACT

An inflatable wrap for promoting venous or arterial blood flow enhancement in the human hand. The wrap comprises an inflatable bag fastened to a backing material. The bag is shaped to fit against the palm of the hand and portions of the back of the hand. The backing material comprises a base portion substantially corresponding to the palm of the hand and two or more interengageable lobes that may be fastened together across the back of the hand to retain the inflatable bag securely against the hand such that upon inflation of the bag a pumping pressure is applied positively to the hand to promote the venous or arterial flow enhancement.

22 Claims, 7 Drawing Sheets

MEDICAL DEVICE FOR THE HAND

FIELD OF THE INVENTION

The present invention relates to medical appliances and more particularly to a novel device for applying local pressure to a portion of the hand for the purpose of stimulating blood circulation through enhanced venous or arterial flow in order to combat such afflictions as ischaemia, pain swelling, algodystrophy and venous thrombosis.

BACKGROUND OF THE INVENTION

A venous pump mechanism is known in the region of the hand essentially including the proximal phalanges of the digits and thumb and the adjacent regions of the palm and dorsum; this mechanism is naturally brought into operation upon a tight doubling of the fist whereupon venous return flow ensues from the entire arm.

It has been established that by periodically squeezing this region without requiring a patient to double his fist, i.e., by external application of squeezing essentially local to this region, venous return flow may be efficiently stimulated even in the case of a degree of venous obstruction in the wrist or elsewhere in the involved arm.

Additionally, it has been established that such externally applied squeezing pressure can also be accompanied by an improvement in arterial flow in the involved arm.

In European Patent No. 0 228 768 there is disclosed an inflatable mitt for engaging the promimal phalanxes of the fingers and thumb of the hand and adjacent regions such that upon periodic pressurization, localized application of a squeezing force may be applied to those parts to stimulate venous flow.

In related European patent application No. 89305062.5 there is disclosed a circumferentially tying inflatable bag shaped for radially inward active engagement solely with a human hand which may be cyclically inflated, the squeezing pressure then being held for a short time to stimulate arterial flow.

A further similar medical appliance is disclosed in "The Return of Blood to the Heart" (Second Edition) by Gardner and Fox (Published by John Libbey), on page 130, FIG. 69 depicts a pneumatically compressible mitten, the mitten body being formed of slitted Neoprene and enclosing an inflation pad wherein Velcro straps are provided externally to direct the force of inflation towards the hand.

All these medical appliances suffer the disadvantage that although an efficacious increase in venous or arterial blood flow is achieved, all require that a glove or mitten-like structure be worn over the affected hand.

In cases to be treated by medical appliances of these types, the affected hand is likely to be painfully swollen and considerably less mobile than usual.

It is, therefore, clear, that where the fingers of the hand must be maneuvered through particular finger holes in a glove, or where the hand must be maneuvered through the appropriate holes in a mitten, the fitting process is likely to be both time consuming from the point of view of the medical practitioner and painful from the point of view of the patient, and may in some cases be impossible.

A further necessity, of course, will be the requirement that a wide range of sizes of such medical appliances be kept to fit the range of sizes of hand encountered, both in terms of normal variation and degree of swelling.

SUMMARY OF THE INVENTION

It is accordingly an object of this invention to provide a medical appliance that will yield an equivalently efficacious promotion of venous or arterial blood flow in an affected hand whilst allowing a considerably improved ease of use both from the point of view of fitting the appliance and adjusting the appliance to the given size of hand.

The above and other features and advantages of the present invention are realized in specific, illustrative embodiments thereof, presented hereinbelow in conjunction with the accompanying drawings, in which.

Figure 6A:
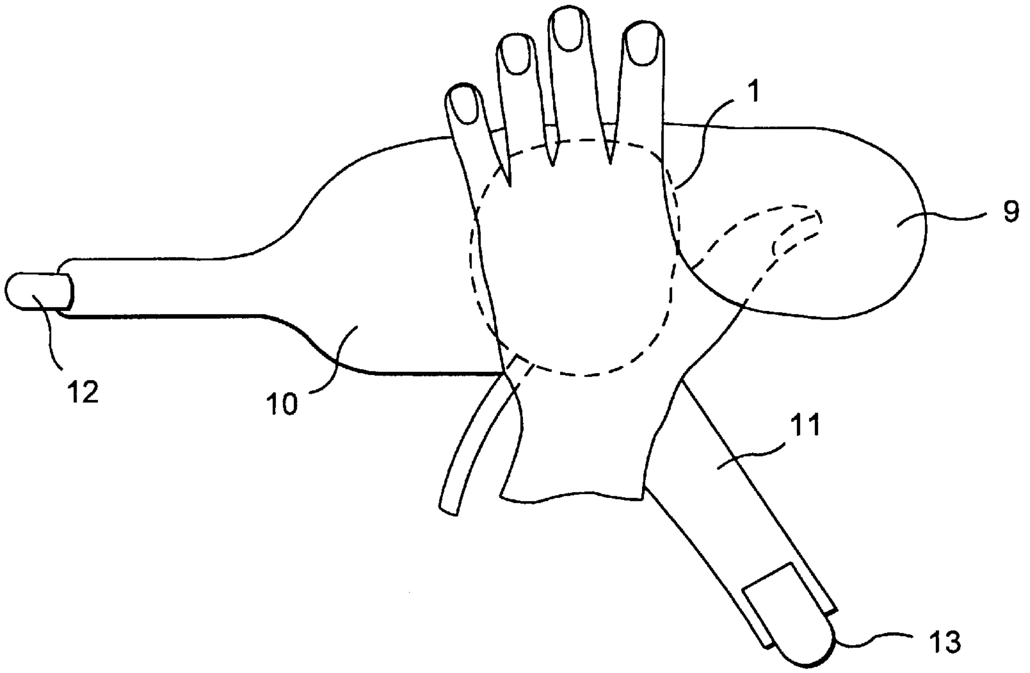
Figure 6B:
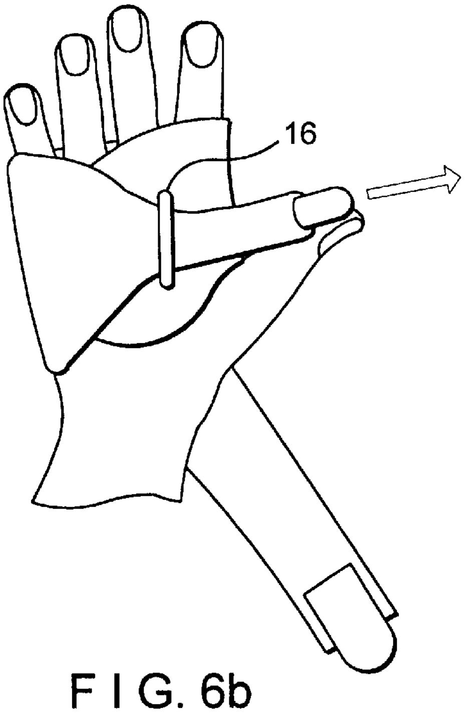
Figure 6C:
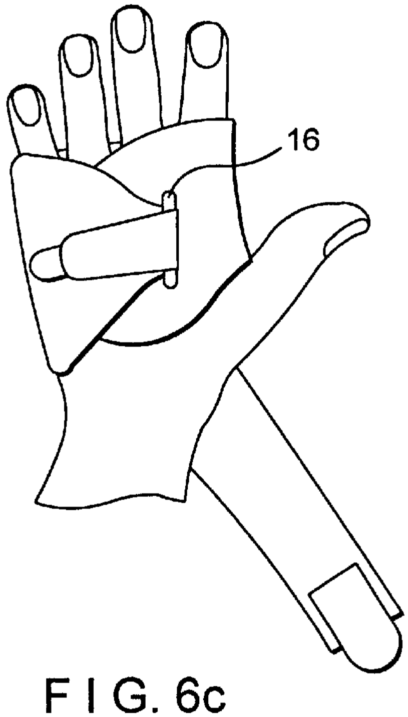
Figure 7:
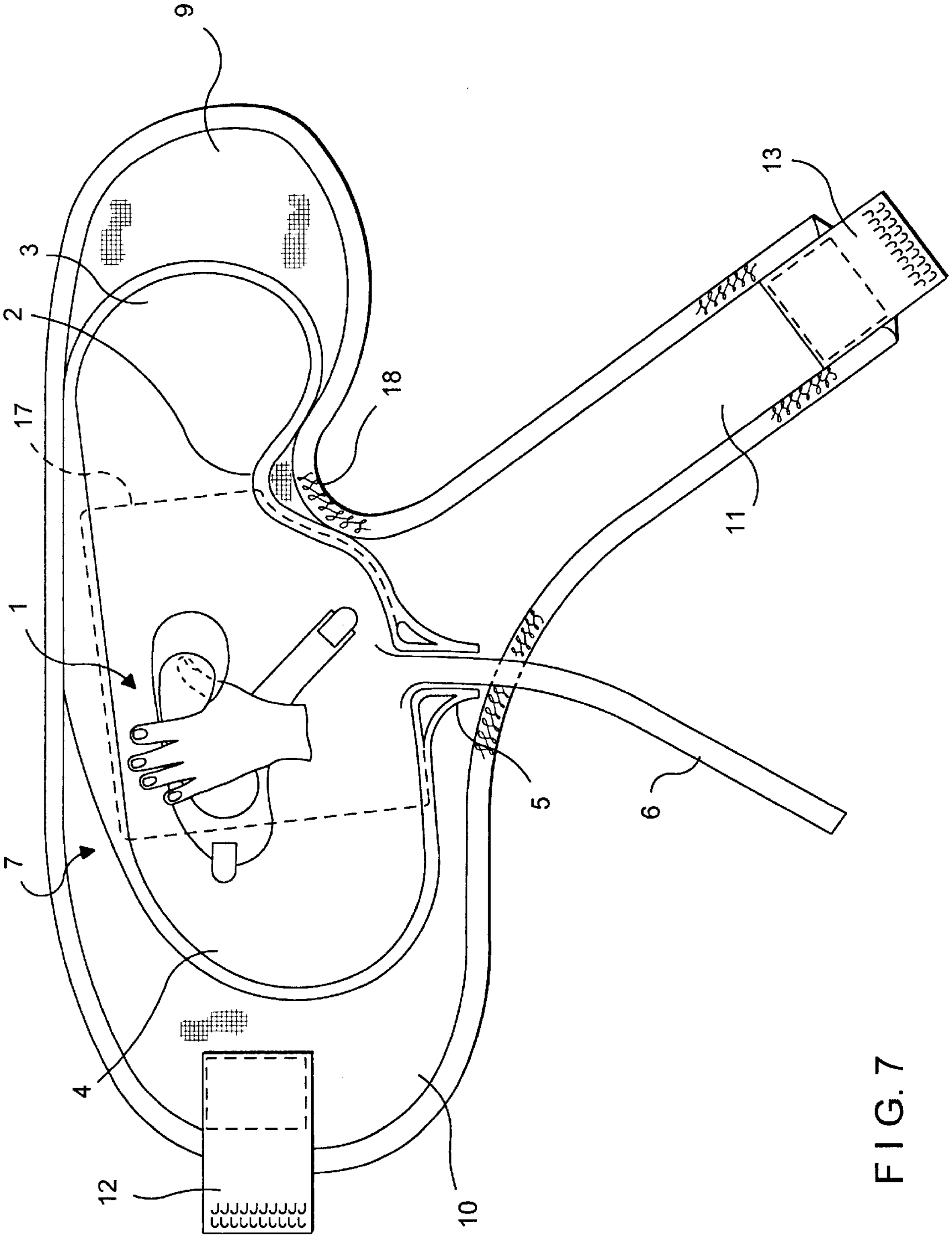
Figure 8:
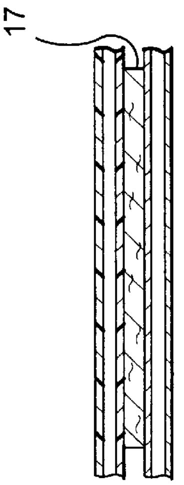
Figure 7A:
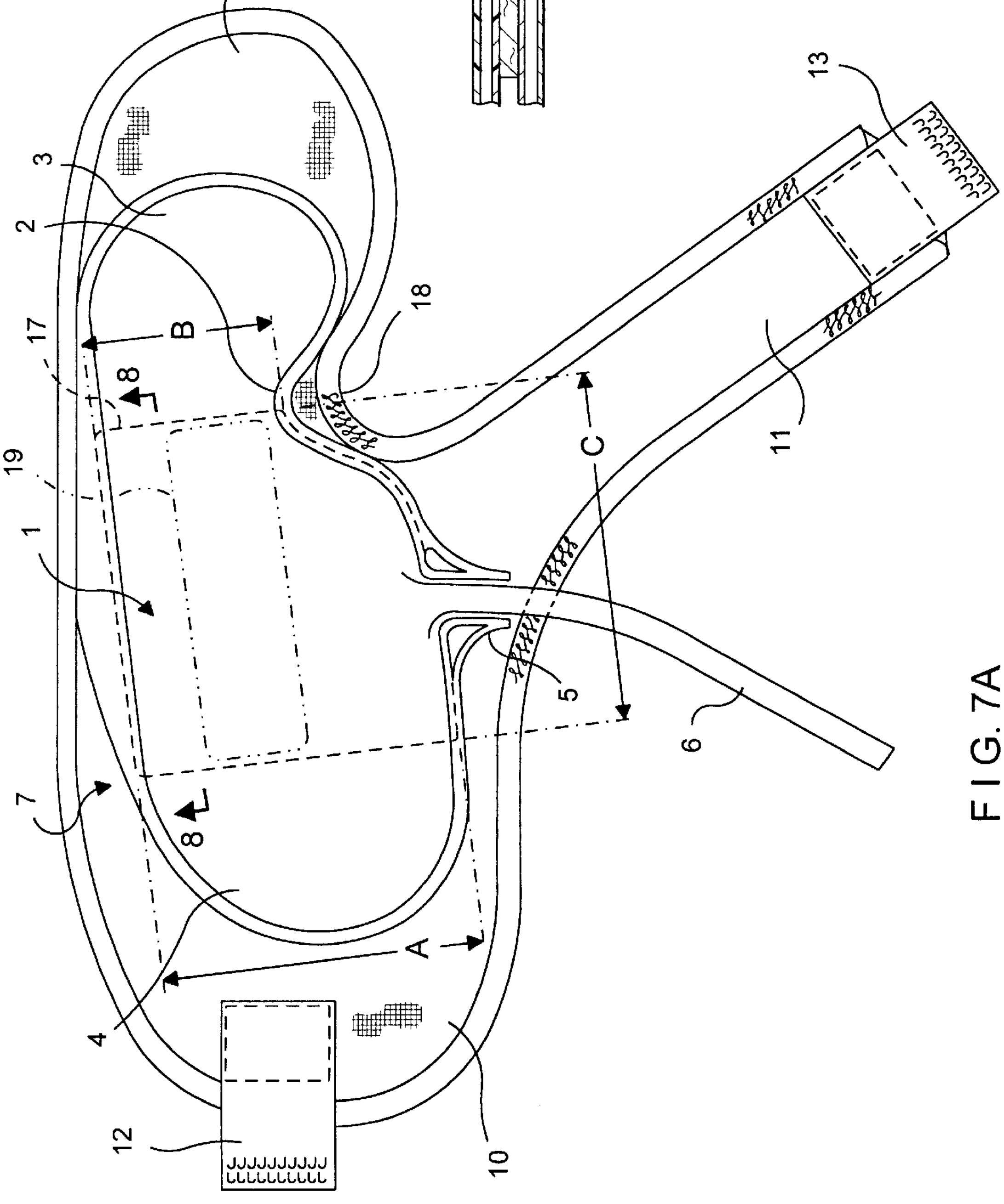

FIGS. 6*a*–6*c* are schematic views of a fourth embodiment of an inflatable hand wrap according to yet another aspect of the present invention;

FIGS. 7 and 7*a* are schematic views of another embodiment of the present invention;

FIG. 8 is a sectional view taken along line 8—8 of FIG. 7A; and

Figure 9:
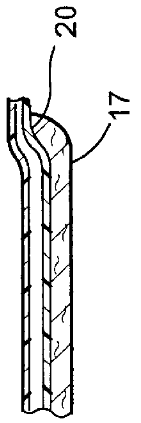

FIG. 9 is a sectional view taken along line 8—8 of FIG. 7A showing flanges along A and B.

The same numerals are used throughout the various figures of the drawings to designate similar parts.

Still other objects and advantages of the present invention will become apparent from the following description of the preferred embodiments.

DESCRIPTION OF THE PREFERRED EMBODIMENTS

Referring now to the drawings and more particularly to FIGS. 1–9 there is shown generally a specific, illustrative medical device for the hand in accordance with various aspects of the present invention.

Figure 1:
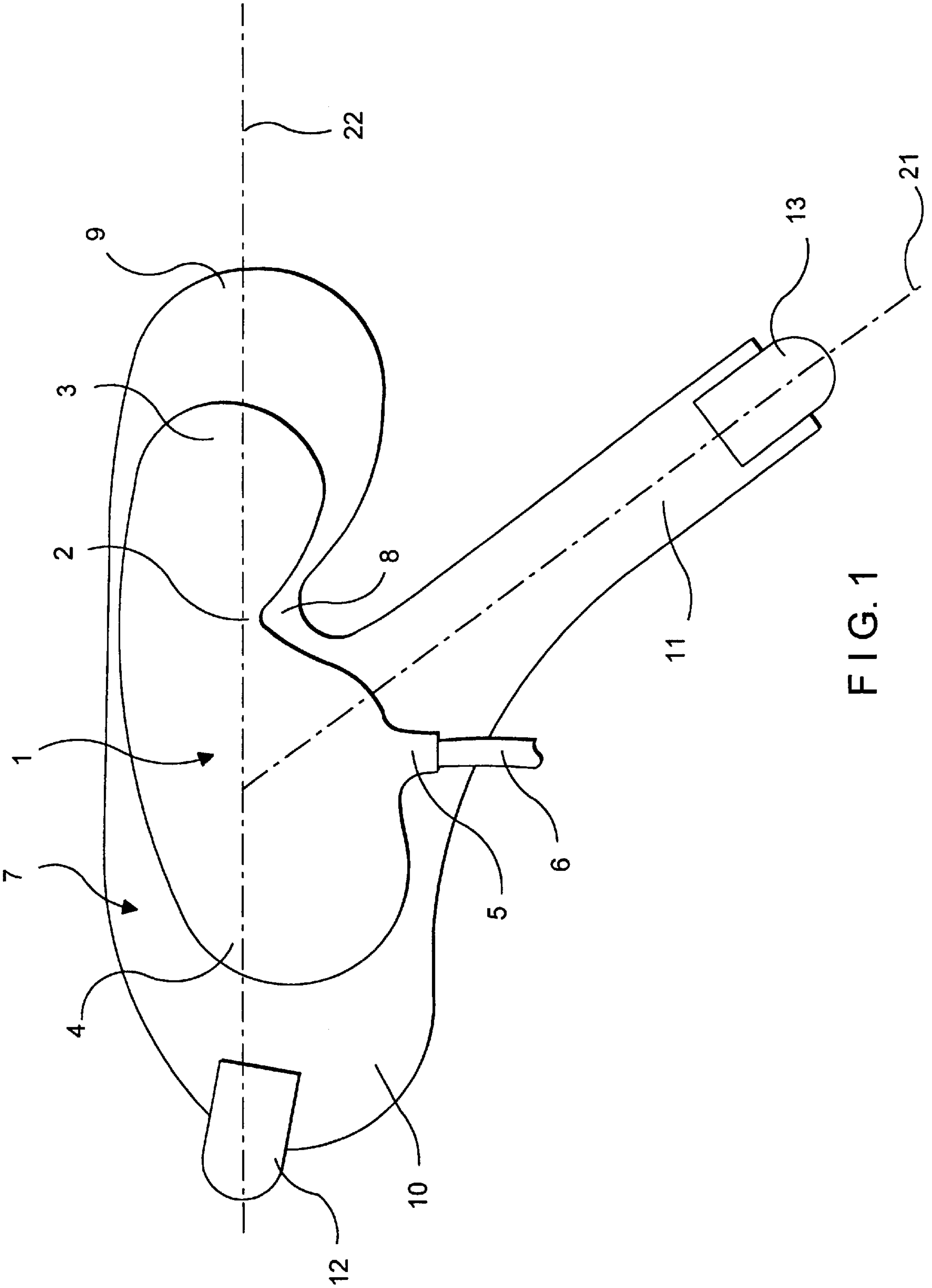
FIG. 1 is a schematic view of a first embodiment of an inflatable wrap according to one aspect of the present invention.
Figure 2:
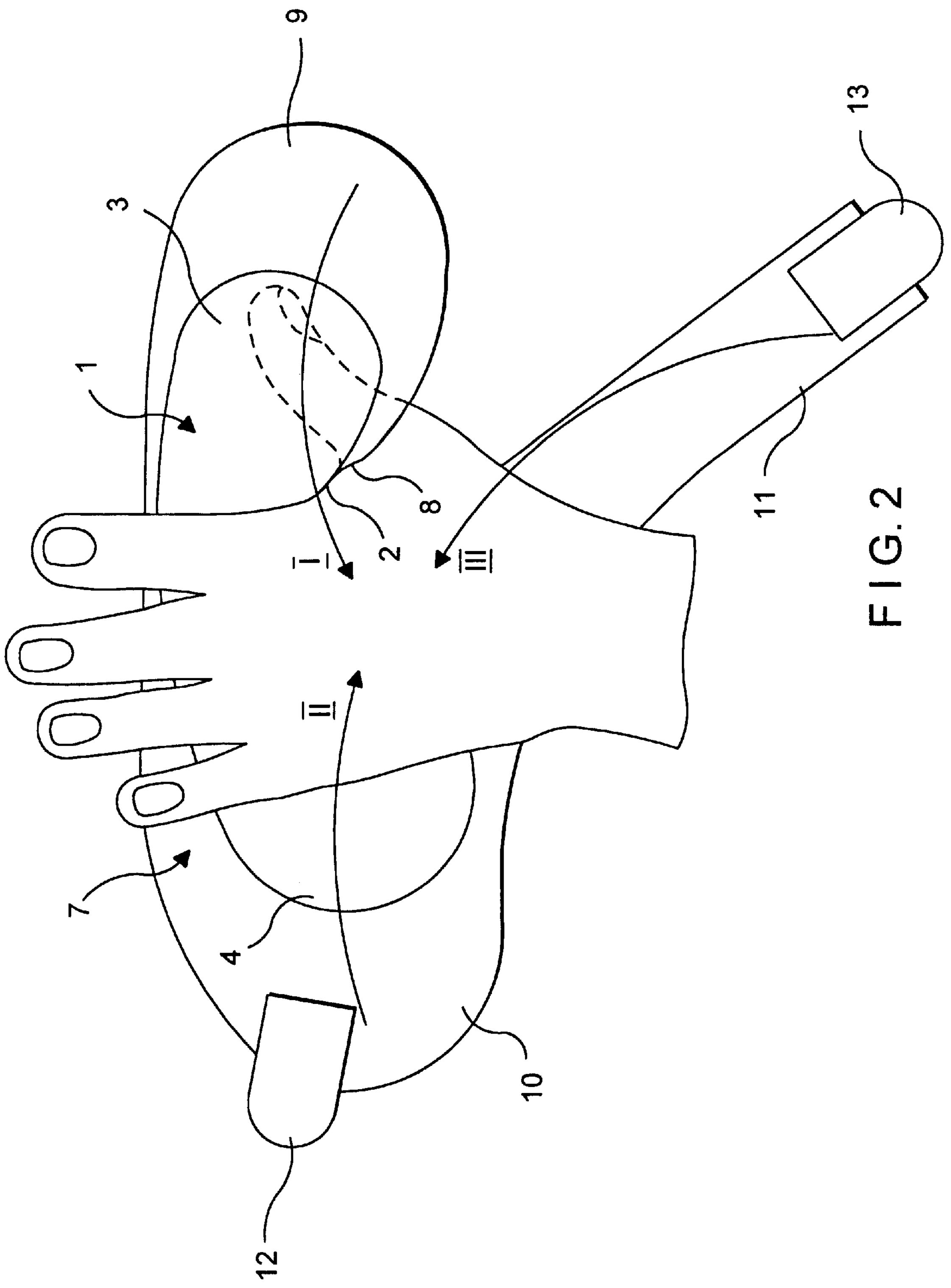
FIG. 2 is a schematic view of a hand placed on the device of FIG. 1 in readiness for the fastening of the device thereabout.

As shown in FIG. 1, the inflatable wrap is provided with an inflatable bag 1 shaped for engagement with the relevant portion of the affected hand when in use. The shaping of the bag includes an indent 2 which is intended to be seated in the portion of the hand between the thumb and the index finger as is indicated in FIG. 2.

The indent 2 defines a right-hand lobe 3 of the inflatable bag 1, with a left-hand lobe 4 defined by the left-most extension of the inflatable bag 1.

The inflatable bag 1 is formed from two portions of a flexible material having appropriate airtightness characteristics which may or may not include ventilation holes (not shown), sealed together on their respective perimeters except for an inlet 5 accepting an associated pressurized air feed 6 allowing the bag 1 to be inflated thereby.

The pressurized air may be fed from a pumping apparatus (not shown) having such operational characteristics as to allow inflation of the bag 1 to the required pressure, typically within two seconds. The inflation/deflation regime is discussed further below.

A base portion of the inflatable bag 1 is secured to an outer material layer 7 by any suitable means, for example sticking with double sided tape or a material such as Velcro, thus allowing repositioning, or by glue bonding to form the inflatable wrap. The form of the outer material layer 7 is also shaped for engagement with the affected hand, and includes an indent 8 corresponding to the inflatable bag indent 2 likewise for seating between the thumb and the index finger of the hand as illustrated in FIG. 2. A right-hand lobe 9 is defined to the right of this indentation 8 with the left-most extension of the outer material layer defining a left-hand lobe 10. A further somewhat longitudinally extended lobe 11 is provided, extending downwardly and to the left of the thumb indentation 8. The extended lobe 11 has a primary axis 21 which intersects and forms an acute angle with a major axis 22 of the right and left hand lobes 9, 10.

The outer material may typically be an inelastic or only slightly elastic material, such as canvas, with an outer looped surface such as brushed nylon for engagement with a material such as Velcro and an inner substantially smooth surface for patient comfort. An intermediate layer of thin foam or cotton wadding may be interposed between the inner surface and the outer material for further patient comfort. All the above layers may be laminated together or joined to one another along their respective perimeters.

The left-hand lobe 10 of the outer material layer 7 and the downwardly extending lobe 11 are furthermore provided with tabs 12, 13 formed of a material such as Velcro which may securely engage the looped surface of the outer material layer 7.

In use, the affected hand is first placed over the device as is indicated in FIG. 2 with the respective indentations 2, 8 seated against the portion of the hand between the thumb and the first finger, such that the thumb of the affected hand passes underneath the right-hand lobe 9 of the outer material layer 7.

The right-hand lobe 9 is folded around the affected hand in the direction of the arrow I, folding substantially along the neck of the lobe 9 thereby guiding the right-hand lobe 3 of the inflatable bag 1 as it moves. The right-hand lobe 3 of the inflatable bag 1 then engages a portion of the back of the hand, being held in place by the overlapping right hand lobe 9 of the outer material layer 7.

The left-hand lobe 10 of the outer material layer 7 is folded over the hand in similar fashion in the direction of the arrow II guiding the left-hand lobe 4 of the inflatable bag 1 into contact with a further portion of the back of the hand. As a result of folding over the respective right and left hand bag lobes 3, 4, the inflatable bag will now substantially circumferentially enclose the affected hand. Due to the greater lateral extent of the right and left hand lobes 9, 10 of the outer material layer 7 these respective lobes 9, 10 will now overlap one another.

Thus the left-hand lobe 10 of the outer material layer 7 may be secured to the underlying right-hand lobe 9 of the outer material layer 7, typically by means of the engagement of the tab 12 with the looped surface of the right-hand lobe 9.

The longitudinally downwardly extended lobe 11 is folded around the base portion of the hand and thumb in the direction of the arrow III, thereby extending diagonally across both the left and right-hand outer material layer lobes 9, 10 whereupon it may be fastened to the outer surface of the left-hand lobe 10, as shown in FIG. 3, again typically by means of engagement of the tab 13 with the looped surface of the outer material layer 7.

Consequently, the affected hand is substantially circumferentially enclosed by the inflatable bag 1 which is secured thereto by means of the interengageable lobes 9, 10 and 11.

Since the lobes 9, 10, and 11 are typically fastened by means of engagement of a tab 12, 13 with a looped surface, the inflatable wrap may easily be adjusted to fit a wide range of sizes of hand.

With the interengagement of the respective three outer material layer lobes 9, 10 and 11, the inflatable wrap effectively encompasses the portion of the hand required to be squeezed whilst allowing free and constant inspection of the fingers and thumb of the affected hand during treatment in respect of, for example, circulation, nerve reaction testing and therapeutic progress in reduction of swelling.

Figure 4:
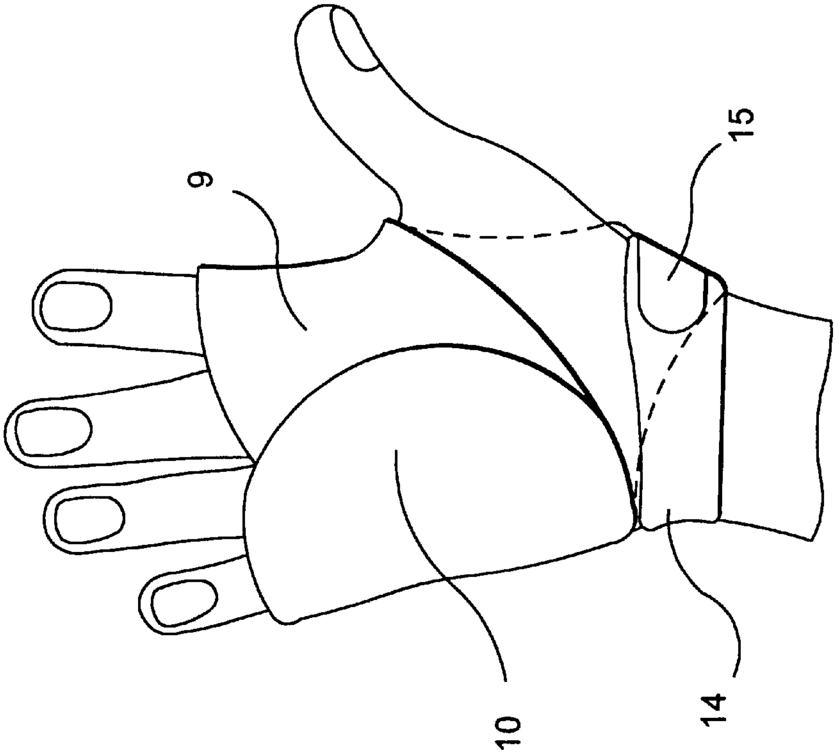
FIG. 4 is a schematic view of an inflatable wrap according to another aspect of the present invention.
Figure 3:
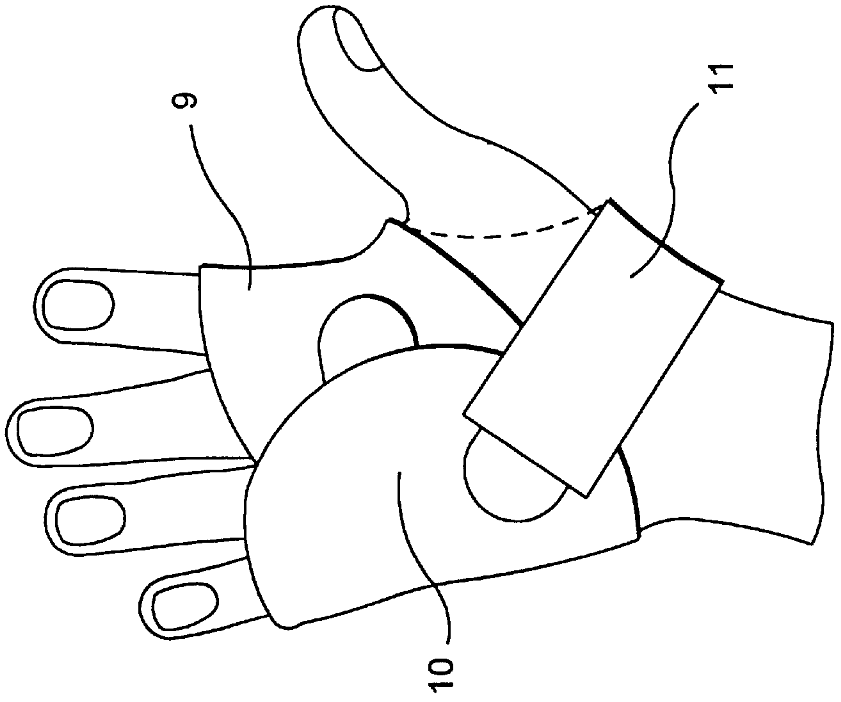
FIG. 3 is a schematic view of the device of FIGS. 1 and 2 fastened around the hand.

In a second embodiment, as shown in FIG. 4, an adjustable wrist strap 14 connected to and extending from the body of the device and tethered around the wrist to itself by means of a tab 15 is used in place of the third lobe 11 to effect the adjustable securing of the inflatable wrap to the hand. Furthermore, in place of the overlap of the respective lobes 9, 10 allowing the interengagement described above, any other suitable means to effect the secure connection of the lobes 9, 10 may be used.

Figure 5:
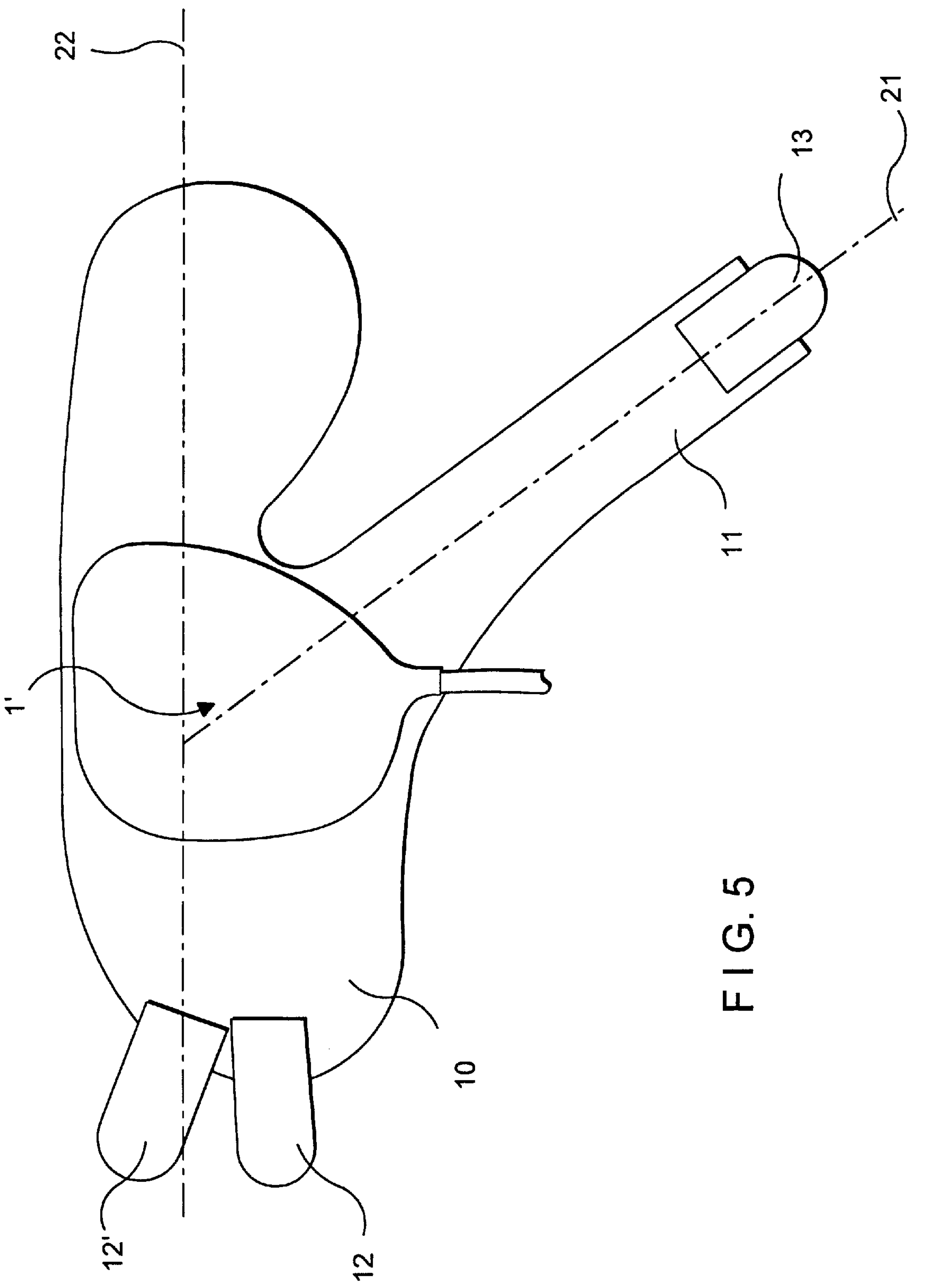
FIG. 5 is a schematic view of an inflatable wrap according to another aspect of the present invention.

If, having regard to a third embodiment, it is simply required to apply the pumping pressure to the palm, then an inflatable bag 1' need only be provided in the region of the palm and the wrap dimensioned accordingly, as indicated generally in FIG. 5. FIG. 5 further displays the provision of a pair of tabs 12, 12' on the left-hand lobe 10. This enables selective tensioning of the wrap and ensures in particular a better fit around the base of the fingers by tensioning the upper (12') of the two tabs.

In the embodiment shown in FIGS. 6*a*, 6*b*, and 6*c* the left-hand lobe 10 of the hand wrap is provided with an extension strapping 10' at the outermost end of which the tab 12 is attached. The underside of the lobe 9 is provided with a loop 16, more clearly shown in FIGS. 6*b* and 6*c*.

As set forth in FIGS. 6*a*, 6*b* and 6*c* the inflatable bladder 1' fits into the palm of the hand. The strapping 10' may either be threaded through the loop 16 when the hand for treatment is laid on the wrap, or it can be passed through the loop 16 before sliding the hand inside the wrap. Pulling on the strapping then provides single handed tensioning of the wrap which is clearly an advantage for persons with a hand disability.

After tensioning, the strapping 10' is folded back upon itself and the tab 12 is attached as by Velcro to the main body of the lobe 10, as shown in FIG. 6*c*. The downwardly extended lobe 11 is folded, as before, around the base portion of the hand and thumb and fastened to the lobe 10.

With a single palm engaging inflatable bladder 1', as shown in FIGS. 5 and 6*a*, 6*b* and 6*c*, the rear of the hand becomes subjected to squeezing forces due to the circumferential nature of the outer wrap, that is through the shrinking of the volume within the wrap, although the inflation in the palm will act to clench the hand into a fist which is the natural mode of action by which blood is pumped from the hand.

The hand wrap may be provided with a pouch in the region of the palm of the hand into which a thin stiffener can be inserted if so desired. This has the effect of maximizing the impulsive pulse delivered to the hand and prevents dissipation of energy.

As shown in FIGS. 7–9, a stiffener panel 17 is positioned between the inflatable bladder and the wrap and secured thereto using suitable fasteners such as Velcro or a double-faced, pressure-sensitive adhesive strip 19. The panel dimensions are designated as A, B and C. Edge portions of the panel may be flanged 20, as illustrated in FIG. 9, according to another embodiment of the present invention. A recess 18 facilitates optimum location of the hand in the wrap.

Having regard to the aforementioned inflation/deflation regime, the therapeutic results obtained after use of the inflatable wrap depend very much on the parameters of the inflation and deflation of the bag.

Where the enhancement of venous return flow is paramount the wrap should be inflated to maximum operational pressure as quickly as possible, typically within two seconds, to imitate the speed with which involved veins are compressionally squeezed in a quick clenching of the fist. Such fast inflation imparts a jerk or sharply pulsed action in return-blood flow, and such action is believed to be helpful in reducing swelling and pain. It is believed that maximum velocity, however transient upon pulsed excitation, is more important than total blood flow. The veins have check-valve formations, and the downstream side of each check-valve is a trap-like situs for undesired accumulation of solids or clotting which may not otherwise be flushed through the venous-return system; it is believed that with bag inflation as rapid as possible, the opening phase for each check value is correspondingly rapid, thus locally stirring trapped return-flow blood and reducing the chances of a clotting constriction of return-flow passages.

The pressure may be released virtually instantaneously after the peak pressure has been achieved, typically in approximately 1 second to minimize patient discomfort, or it may be held on for typically up to about 4 seconds where maximal hyperaemia and arterial inflow is desired. After the pressure has been released, a period is allowed for the refilling of the veins prior to the application of the next pressure cycle and this may typically be generally within a range of 5 and 30 seconds.

The peak pressure P for any delivered inflation impulse should be that which is sufficient to produce the appropriate venous impulse, typically between about 50 and about 300 mm of Hg, whilst not being too uncomfortable for the patient to tolerate. This will, of course, mean a peak pressure P which will vary, depending upon the particular patient and his affliction.

Furthermore, the walls of the vessels produce EDRF (Endothelial-derived relaxing factor, believed to be nitrous oxide) in response to shear stress produced by changes of blood flow. The EDRF so released plays a role both in powerfully relaxing vessel wall muscle thereby allowing increase a blood flow and desegregating platelets further helping to explain how such impulse pumping is effective in preventing, for example, venous thrombosis. It is believed that the maximal shear stress is achieved by the maximal acceleration from the surge of blood as a result of the applied pumping pressure.

For arterial flow enhancement however if, following the inflation the local compression is held for a period of typically up to about five seconds, a therapeutically beneficial result is achieved in arm-artery afflictions which involve ischaemia from various causes that have produced arterial obstruction in an extremity.

The effect is maximized for any given patient by selecting the maximum pressure P which the particular patient can comfortably tolerate.

Since from the foregoing the construction and advantages of the invention may be readily understood, further explanation is believed unnecessary. However, since numerous modifications will readily occur to those skilled in the art after consideration of the foregoing specification and accompanying drawings, it is not intended that the invention be limited to the exact construction shown and described, but all suitable modifications and equivalents may be resorted to which fall within the scope of the appended claims.

What is claimed is:

1. A medical device for applying a venous or arterial blood flow enhancement pumping pressure to a human hand, comprising an inflatable sealed enclosure for engagement with the hand and means for selective admission of inflation pressure fluid into the enclosure to apply the pumping pressure to the hand, characterized by means for securing the enclosure to the hand to form an inflatable wrap adapted to envelope the hand with the fingers and thumb adapted to extend from the wrap during use such that the distal ends of the fingers are separated by the wrap from the thumb, said securing means having two lobes defining a peripheral extent including an indent formed adjacent to and between said two lobes, said two lobes being connectable to each other such that the thumb of the hand is received and located in said indent on one side of the wrap and the palm and adjacent proximal phalanges of the hand are on the other side of the wrap, said connection of said two lobes acting to retain the wrap on the hand such that on inflation of the enclosure, a squeezing action is applied to promote venous or arterial blood flow.

2. The medical device set forth in claim 1 wherein the inflatable sealed enclosure is adapted to be placed in a retained position in which the inflatable sealed enclosure substantially circumferentially encloses the hand.

3. The medical device set forth in claim 1 wherein the retained position the inflatable sealed enclosure substantially engages only the palm of the hand.

4. The medical device set forth in claim 1 wherein the two lobes are connectable to each other by means of providing one lobe with a tab, the other lobe having an outer surface engageable by said tab to permit adjustable attachment of said tab to said outer surface.

5. The medical device set forth in claim 4 wherein the one lobe is provided with one or more further tabs for adjustable attachment to the other lobe.

6. The medical device set forth in claim 1 wherein the two lobes are connected to each other by a means of providing one lobe with an elongate strap which can be threaded through a loop provided on the outer surface of the other lobe and then back upon itself for engagement with the other surface of the one lobe, thereby to permit selective tensioning of the wrap around the hand.

7. The medical device set forth in claim 1 wherein the securing means includes a third lobe for adjustable attachment around the base of the thumb of the hand to one or both of the first and second lobes.

8. The medical device set forth in claim 7 wherein the third lobe is adjustably attached to one or both of the first and second lobes by means of providing the third lobe with a tab which engages the outer surface of the respective lobes to allow adjustable attachment.

9. The medical device set forth in claim 1 wherein the securing means includes a strap for securable attachment around the wrist.

10. The medical device set forth in claim 1 wherein the sealed enclosure is a bag fastened to a backing material having a peripheral extent in excess of that of the bag, said backing material having a contour in which said indent is formed, said indent having a U-shape, the contour of said bag having a corresponding U-shaped indent such that said indents together provide a thumb insert.

11. The medical device set forth in claim 1 wherein a pouch is provided for accepting a stiffener whereby to maximize the impulse delivered to the hand during pumping of the inflatable sealed enclosure.

12. The medical device set forth in claim 1 including means for cyclically inflating the sealed enclosure between a peak operating pressure achieved within about 2 seconds and a minimum operating deflation pressure achieved generally within a range of 5–30 seconds of the peak pressure.

13. The medical device set forth in claim 12 wherein the peak operating pressure is held for up to about 5 seconds before release.

14. The medical device set forth in claim 13 wherein the peak pressure is generally within a range of 50 and 300 mm Hg.

15. A medical device for applying a venous or arterial blood flow enhancement pumping pressure to a human hand, comprising an inflatable sealed enclosure for engagement with the hand and means for selective admission of inflation pressure fluid into the enclosure to apply the pumping pressure to the hand, characterized by means for securing the enclosure to the hand to form an inflatable wrap adapted to envelope the hand with the fingers and thumb adapted to extend from the wrap during use such that the distal ends of the fingers are separated by the wrap from the thumb, said securing means having two lobes defining a peripheral extent including an indent formed adjacent to and between said two lobes, said two lobes being connectable to each other such that the thumb of the hand is received and located in said indent on one side of the wrap and the palm and adjacent proximal phalanges of the hand are on the other side of the wrap, said connection of said two lobes acting to retain the wrap on the hand such that on inflation of the enclosure, a squeezing action is applied to promote venous or arterial blood flow, the inflatable wrap further comprising a stiffener secured thereto for maximizing the impulse delivered to the hand during pumping.

16. A medical device for applying a venous or arterial blood flow enhancement pumping pressure to a human hand, comprising an inflatable sealed enclosure for engagement with the hand and means for selective admission of inflation pressure fluid into the enclosure to apply the pumping pressure to the hand, characterized by means for securing the enclosure to the hand to form an inflatable wrap adapted to envelope the hand with the fingers and thumb adapted to extend from the wrap during use such that the distal ends of the fingers are separated by the wrap from the thumb, said securing means having two lobes which are connectable to each other and which act to retain the wrap on the hand such that on inflation of the enclosure, a squeezing action is applied to promote venous or arterial blood flow, the inflatable wrap further comprising a stiffener secured thereto for maximizing the impulse delivered to the hand during pumping, said stiffener having edge portions which are flanged so as to concentrate the impulse delivered to the hand during pumping.

17. A medical device for applying a venous or arterial blood flow enhancement pumping pressure to a human hand, comprising an inflatable sealed enclosure for engagement with the hand and means for selective admission of inflation pressure fluid into the enclosure to apply the pumping pressure to the hand, characterized by means for securing the enclosure to the hand to form an inflatable wrap adapted to envelope the hand with the fingers and thumb adapted to extend from the wrap during use such that the distal ends of the fingers are separated by the wrap from the thumb, said securing means having two lobes which are connectable to each other and which act to retain the wrap on the hand such that on inflation of the enclosure, a squeezing action is applied to promote venous or arterial blood flow, the inflatable wrap having a finger recess adjacent to and between said two lobes such that the thumb of the hand is received and located in said finger recess on one side of the wrap and the palm and adjacent proximal phalanges of the hand are on the other side of the wrap for optimum location of the hand in the wrap.

18. A medical device for applying a venous or arterial blood-flow enhancing pressure to a patient's hand, comprising an inflatable sealed enclosure adapted for engagement with at least adjacent regions of the palm and proximal phalanges of the hand and means for selective admission of pulsed inflation pressure and means for selective admission of pulsed inflation pressure into the inflatable enclosure to apply the pumping pressure to the hand, wrapping means for securing the inflatable enclosure to the hand, said wrapping means having a peripheral contour with a local recess adjacent to and between first and second lobe formations of the peripheral contour of said wrapping means, said local recess being adapted to receive and locate the thumb of the hand on one side of the wrapping means and the palm and adjacent proximal phalanges of the hand on the other side of the wrapping means, said first and second lobe formations being adapted for completion of a circumferentially secured tie of said lobe formations to each other over the closure of the hand, with other phalanges of the fingers of the hand projecting externally of said wrapping means, and the peripheral contour of said wrapping means further including a third lobe extending in the direction between the patient's thumb and wrist, said third lobe being adapted to further complete a secured tie of said third lobe to one of said first and second lobes and around a proximal phalange portion of the thumb.

19. The medical device set forth in claim 18, wherein a stiffening panel is carried by said wrapping means in lapped register with said inflatable enclosure and limited by the transverse span (C) of the palm of the hand.

20. A medical device for applying a venous or arterial blood-flow enhancing pressure to a patient's hand, comprising an inflatable sealed enclosure adapted for engagement with at least adjacent regions of the palm and proximal phalanges of the hand and means for selective admission of pulsed inflation pressure and means for selective admission of pulsed inflation pressure into the inflatable enclosure to apply the pumping pressure to the hand, wrapping means for securing the inflatable enclosure to the hand, said wrapping means having a peripheral contour with a local recess adapted to receive and locate the thumb of the hand on one side of the wrapping means and the palm and adjacent proximal phalanges of the hand on the other side of the wrapping means, the peripheral contour of said wrapping means having first and second lobe formations adapted for completion of a circumferentially secured tie of said lobe formations to each other over the closure of the hand, with other phalanges of the fingers of the hand projecting externally of said wrapping means, and the peripheral contour of said wrapping means further including a third lobe extending in the direction between the patient's thumb and wrist, said third lobe being adapted to further complete a secured tie of said third lobe to one of said first and second lobes and around a proximal phalange portion of the thumb, a stiffening panel being carried by said wrapping means in lapped register with said inflatable enclosure and limited by the transverse span (C) of the palm of the hand, the stiffening panel including a stiffening flange formation.

21. A medical device for applying a venous or arterial blood-flow enhancing pressure to a patient's hand, comprising an inflatable sealed enclosure adapted for engagement with at least adjacent regions of the palm and proximal phalanges of the hand and means for selective admission of pulsed inflation pressure and means for selective admission of pulsed inflation pressure into the inflatable enclosure to apply the pumping pressure to the hand, wrapping means for securing the inflatable enclosure to the hand, said wrapping means having a peripheral contour with first and second lobe formations adapted for completion of a circumferentially secured tie of said lobe formations to each other over the closure of the hand, with other phalanges of the fingers of the hand projecting externally of said wrapping means, said first and second lobes having a major axis, and the peripheral contour of said wrapping means further including a third lobe extending in the direction between the patient's thumb and wrist, said third lobe having a primary axis and oriented relative to said first and second lobes such that said major and primary axes intersect and form an acute angle, said third lobe being adapted to further complete a secured tie of said third lobe to one of said first and second lobes and around a proximal phalange portion of the thumb.

22. The medical device set forth in claim 21, wherein said peripheral contour of said wrapping means has a local recess adjacent to and between said first and second lobes, said local recess being adapted to receive and locate the thumb of the hand on one side of the wrapping means and the palm and adjacent proximal phalanges of the hand on the other side of the wrapping means.

* * * * *